(12) United States Patent
Goldberg et al.

(10) Patent No.: US 7,979,258 B2
(45) Date of Patent: Jul. 12, 2011

(54) SELF-CALIBRATION OF MASS SPECTRA USING ROBUST STATISTICAL METHODS

(75) Inventors: David Goldberg, Palo Alto, CA (US); Marshall Bern, San Carlos, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 713 days.

(21) Appl. No.: 11/017,383

(22) Filed: Dec. 20, 2004

(65) Prior Publication Data

US 2006/0136158 A1 Jun. 22, 2006

(51) Int. Cl.
 *G06G 7/48* (2006.01)
 *G01N 33/48* (2006.01)
 *G01N 31/00* (2006.01)
 *G06F 19/00* (2011.01)

(52) U.S. Cl. ................ 703/11; 702/19; 702/22; 702/27

(58) Field of Classification Search .................. None
 See application file for complete search history.

(56) References Cited

U.S. PATENT DOCUMENTS

| 6,365,893 B1 | 4/2002 | Le Cocq |
| 6,590,204 B2 | 7/2003 | Baranov |

OTHER PUBLICATIONS

Aebersold et al. "Mass Spectromtery-based Proteomics" Nature (Mar. 2003) vol. 422, pp. 198-207.*
Horn et al. "Automated Reduction and Interpretation of High Resolution Electrospray Mass Spectra of Large Molecules" J. Am. Soc. Mass Spectrom (2000) vol. 11, pp. 320-332.*
Anderson et al., "Proteomic characterization of the human centrosome . . . ," Nature, 426, pp. 570-574 (2003).
Gras et al., "Improving Protein Identification . . . ," Electrophosesis 20 3535-3550 (1999).
Chernushevich et al., "An Introduction . . . ," J Mass Spectrom., 2001 (36): 849,865.
Taylor et al., "Implementation . . . ," Analytical Chemistry, vol. 73, No. 11, (2001), 2594-2604.
Fischler et al., "Random Sample Consensus: A Paradigm for Model Fitting . . . ," Communication sof the ACM, vol. 24 No. 6, (1981), pp. 381-395.
EP Search Report, EP Application No. 05112476.6-1232/1672673; dated Jun. 30, 2010, Completed May 26, 2010; the Hague.
Christian et al., "Improved Calibration of Time of Flight Mass Spectra by Simplex Optimization of Electrostatic Ion Calculations", Analytical Chemistry, American Chemical Society, US, vol. 72, No. 14, pp. 3327-3337; Jul. 15, 2000.
Press et al., "Chapter 15: Modeling of Data", Numerical Recipes in C: The Art of Scientific Computing, 1992, Cambridge University Press, Cambridge, UK, pp. 656-706.
Pop et al., "A New Fuzzy Regression Algorithm", Analytical Chemistry, vol. 68, No. 5, Mar. 1, 1996, pp. 771-778, Washington, D.C. US.

* cited by examiner

*Primary Examiner* — Eric S DeJong
(74) *Attorney, Agent, or Firm* — Fay Sharpe LLP

(57) ABSTRACT

The use of a robust statistical method for self-calibration of a measuring instrument, such as a mass spectrometer, is disclosed. The method involves the use of differences in mass and complementary pairs for example, to estimate calibration parameters. Self-calibration of various mass spectra is described. Related systems and computer-readable media are also described.

27 Claims, 11 Drawing Sheets

SELF-CALIBRATION OF MASS SPECTRA USING ROBUST STATISTICAL METHODS

STATEMENT REGARDING FEDERALLY SPONSORED RESEARCH OR DEVELOPMENT

This invention was made with Government support under NIH Grant No. 5 U54 GM062116-04. The Government has certain rights in this invention.

BACKGROUND

The present exemplary embodiment relates to the use of robust statistical methods in recalibrating measured mass spectra so that measured masses are transformed to be closer to true masses. It finds particular application in conjunction with calibration techniques for mass spectrometry, and will be described with particular reference thereto. However, it is to be appreciated that the present exemplary embodiment is also amenable to other like applications.

The preferred technique for identifying and analyzing biological macromolecules such as peptides and glycans is mass spectrometry (MS). A mass spectrometer is a device able to volatilize/ionize analytes to form vapor-phase ions and determine their absolute or relative molecular masses. A mass spectrometer is generally comprised of at least one ion source, at least one mass analyzer, and at least one detector, though this number of and these particular components are exemplary and not intended to be limiting in any way. Ion sources use methods including, but not limited to, electron bombardment, electrospray ionization, matrix-assisted laser desorption/ionization (MALDI), atmospheric pressure chamber ionization (ACPI), fast atom bombardment, chemical ionization, inductively coupled plasma, and the like or combinations thereof. Mass analyzers use methods including, but not limited to, Fourier transform mass spectrometry (FTMS), quadrupole time-of-flight (QTOF), ion trap, and triple quadrupole. Detectors use methods including, but not limited to, electron multiplication and photon multiplication. Consequently, many permutations of mass spectrometers exist. Those of ordinary skill in the art will recognize these and other types of mass spectrometers, the various methods and theories behind which they operate, and the advantages and disadvantages of the various permutations. The present exemplary embodiment is intended to apply to mass spectra generated by all types of mass spectrometers, with particular application to spectra generated by TOF mass spectrometers. Mass spectrometers may also be hooked up in tandem, the output of the first mass spectrometer being used as the input for the second mass spectrometer; this is known as tandem MS or MS/MS. Further information on mass spectrometry can be found in the *Encyclopedia of Chemical Technology*, Vol. 15, 4$^{th}$ ed., "Mass Spectrometry", (1995), and *Mass Spectrometry: Principles and Applications*, Hoffman et. al., Wiley (1996), the entire contents of both being incorporated by reference herein.

A mass spectrometer measures the mass-to-charge ratio (m/z) of ions. The resulting mass spectrum is plotted as a graph of relative intensity versus m/z. As used herein, a mass spectrum can be the product of either a single mass spectrometer or of a tandem mass spectrometer. It should be noted that the terms peak, m/z, and mass have been used interchangeably in the art even though they do not possess equal dimensional units; however, mass is usually distinguished from m/z. With the mass spectrum and other known data, such as its atomic formula and/or molecular weight, the sample macromolecule can be identified and/or analyzed.

A tandem mass spectrometer fragments ions of selected m/z and measures the m/z of the resulting fragment ions. When the ion is a peptide the fragment is termed a "peptide fragment." For peptides the most common fragment ions are designated as a-, b-, c-, x-, y-, or z-ions depending on which peptide bond is broken and on which side of the bond the ionic charge is located. When the peptide sequence is written conventionally from N-terminus to C-terminus, a-, b-, and c-ions refer to those fragments including the N-terminus; x-, y-, and z-ions refer to those fragments including the C-terminus. Fragments resulting from a single break in the peptide are called complementary. For example, the $b_3$ ion for the peptide AEFVEVTK is AEF; the complementary $y_5$ ion is VEVTK. a-, b-, c- ions can be distinguished from x-, y-, z-ions by selectively labeling or substituting one end of the peptide, for example by replacing $^{16}O$ in the terminal acid at the C-terminus with the isotope $^{18}O$. This change can be detected and seen in the resulting mass spectrum. In addition, ions are labeled as "parent" ions when they are further fragmented into shorter "daughter" ions.

A mass spectrometer only measures the m/z ratio and hence further work must be done to identify the sample macromolecule. Some factors may be relevant to the identification process. Ionized fragments can further dissociate, for example by losing molecules such as carbon monoxide, water, and ammonia. It should also be noted that isotopes of atoms occur naturally, for example $^{12}C$ and $^{13}C$. These isotopes result in fragments with the same chemical formula but different masses. The various combinations of isotopes possible in an ion create what is called an isotope envelope, where the spacing of peaks and their relative heights due to the natural abundance of isotopes can be predicted. Ions can also be multiply charged; for example, a doubly charged ion can often be recognized by the ½ Dalton (Da) spacing of their accompanying isotope peaks, whereas a triply charged ion can often be recognized by a ⅓ Dalton spacing etc. instead of the normal 1 Dalton spacing for singly charged ions.

The identification of a sample macromolecule depends upon assigning identifications to the peaks in the spectrum. Reliable peak identifications critically depend upon the accuracy of the mass measurement. For example, a peak at m/z 378.83 does not match a b-ion of KHL (mass 379.24) if the measurement uncertainty is plus or minus 0.02, but does match if the measurement uncertainty is 0.5. The larger the measurement uncertainty, the greater the chance of a false assignment and a subsequent failure of identification.

Measurement uncertainty is minimized by accurate estimation of the bias and the precision of the spectrometer. As one of ordinary skill in the art knows, there is a maximum precision inherent to the type of instrument used; for example, FTMS has a precision of 1-2 ppm (0.001 Da at a typical m/z of 1000 Da) and QTOF has a nominal precision of 10 ppm (0.01 Da). However, the precision can also vary depending upon the instrument set-up. The parameters that correct for bias can also vary between set-ups and even between spectra. An example is provided in FIGS. 1 and 2, which show two mass spectra taken at different times on the same TOF instrument from the same sample. The two graphs plot deviation (observed mass minus theoretical mass) versus the measured mass of the peak. In each case the deviation varies linearly with the mass of the peak. A linear fit is shown and it is clear that the bias (the slope of the line) is quite different (note the difference between the y-axes on the two graphs) even though the precision (closeness of points to the line) is similar.

The traditional technique for achieving the theoretical instrument precision is "internal calibration," meaning the inclusion of a calibrant molecule such as polypropylene glycol in the sample. Several calibrant molecules and methods of their use are known. However, they all suffer from the same drawbacks. First, calibrant molecules give only a limited number of peaks for calibration. Second, there is the chance that calibrant peaks will obscure or diminish signal peaks.

The present exemplary embodiment contemplates a new and improved calibration method, related systems, and media, which overcome the above-referenced problems and others.

BRIEF DESCRIPTION

In a first aspect of the present exemplary embodiment, a method is provided for providing a recalibrated mass spectrum of a sample including a plurality of macromolecules. The method comprises obtaining a mass spectrum of the plurality of macromolecules. The mass spectrum contains a plurality of peaks each of which corresponds to a mass-to-charge ratio. The method also comprises selecting a plurality of predetermined molecules appropriate to the sample. The method further comprises creating a data set comprising a subset of the plurality of peaks wherein each peak in the subset of the plurality of peaks is assigned to one or more of the plurality of predetermined molecules. The method also comprises applying a robust statistical method to the data set to calculate at least one transformation parameter. And, the method comprises transforming the mass spectrum by using at least one of the transformation parameters to thereby provide the recalibrated mass spectrum.

In another aspect, the present exemplary embodiment provides a method for providing a recalibrated mass spectrum of a sample including a plurality of macromolecules. The method comprises obtaining a mass spectrum of the plurality of macromolecules. The mass spectrum contains a plurality of peaks each of which correspond to a mass-to-charge ratio. The method also comprises selecting a. plurality of predetermined molecules appropriate to the sample. The method further comprises creating a data set comprising a plurality of peak pairs from the plurality of peaks wherein each of the peak pairs is assigned to one of the plurality of predetermined molecules. The method also comprises applying a robust statistical method to the data set to calculate at least one transformation parameter. And, the method comprises transforming the mass spectrum by using the at least one transformation parameter to thereby provide the recalibrated mass spectrum.

In another aspect, the present exemplary embodiment provides a system for providing a recalibrated mass spectrum of a sample including a plurality of macromolecules. The system comprises a first storage device operative to maintain a mass spectrum. The mass spectrum contains a plurality of peaks, each of the plurality of peaks corresponding to a mass-to-charge ratio. The system also comprises a second storage device operative to maintain computer-executable instructions including a computer program to (i) select a plurality of predetermined molecules appropriate to the sample, (ii) create a data set comprising a subset of the plurality of peaks wherein each peak of the subset of the plurality of peaks is assigned to one or more of the plurality of predetermined molecules, (iii) apply a robust statistical method to the data set to calculate at least one transformation parameter, and (iv) transform the mass spectrum by using the at least one transformation parameter to thereby provide the recalibrated mass spectrum. The system also comprises a processor in communication with the first and second storage devices and operative to execute the computer program to thereby provide the recalibrated mass spectrum.

In another aspect, the present exemplary embodiment provides a system for providing a recalibrated mass spectrum of a sample including a plurality of macromolecules. The system comprises a first storage device operative to maintain a mass spectrum including a plurality of peaks corresponding to a mass-to-charge ratio. The system also comprises a second storage device operative to maintain computer-executable instructions including a computer program to (i) select a plurality of predetermined molecules appropriate to the sample, (ii) create a data set comprising a plurality of peak pairs from the plurality of peaks wherein each of the peak pairs is assigned to one of the plurality of predetermined molecules, (iii) apply a robust statistical method to the data set to calculate at least one transformation parameter, and (iv) transform the mass spectrum by using the at least one transformation parameter to thereby provide the recalibrated mass spectrum. The system also comprises a processor in communication with the first and second storage devices and operative to run the computer program to thereby provide the recalibrated mass spectrum.

In a further aspect, the present exemplary embodiment provides a computer-readable medium having computer-executable instructions for performing a method comprising obtaining a mass spectrum of the plurality of macromolecules. The mass spectrum contains a plurality of peaks, each of which corresponds to a mass-to-charge ratio. The method also comprises selecting a plurality of predetermined molecules appropriate to the sample. The method further comprises creating a data set comprising a subset of the plurality of peaks wherein each peak of the subset of the plurality of peaks is assigned to one or more of the plurality of predetermined molecules. The method further comprises applying a robust statistical method to the data set to calculate at least one transformation parameter. And, the method comprises transforming the mass spectrum by using the at least one transformation parameter to thereby provide the recalibrated mass spectrum.

In yet another aspect, the present exemplary embodiment provides a computer readable medium having computer executable instructions for performing a method comprising obtaining a mass spectrum of a plurality of macromolecules. The mass spectrum contains a plurality of peaks each of which corresponds to a mass-to-charge ratio. The method comprises selecting a plurality of predetermined molecules appropriate to the sample. And, the method comprises creating a data set comprising a plurality of peak pairs from the plurality of peaks wherein each of the peak pairs is assigned to one of the plurality of predetermined molecules. The method further comprises applying a robust statistical method to the data set to calculate at least one transformation parameter. And, the method comprises transforming the mass spectrum by using the at least one transformation parameter to thereby provide the recalibrated mass spectrum.

One advantage of the present exemplary embodiment is that signal peaks are not obscured, diminished, or otherwise changed.

Another advantage of the present exemplary embodiment is improved precision and consequently improved identification of sample macromolecules.

DETAILED DESCRIPTION

Figure 1:
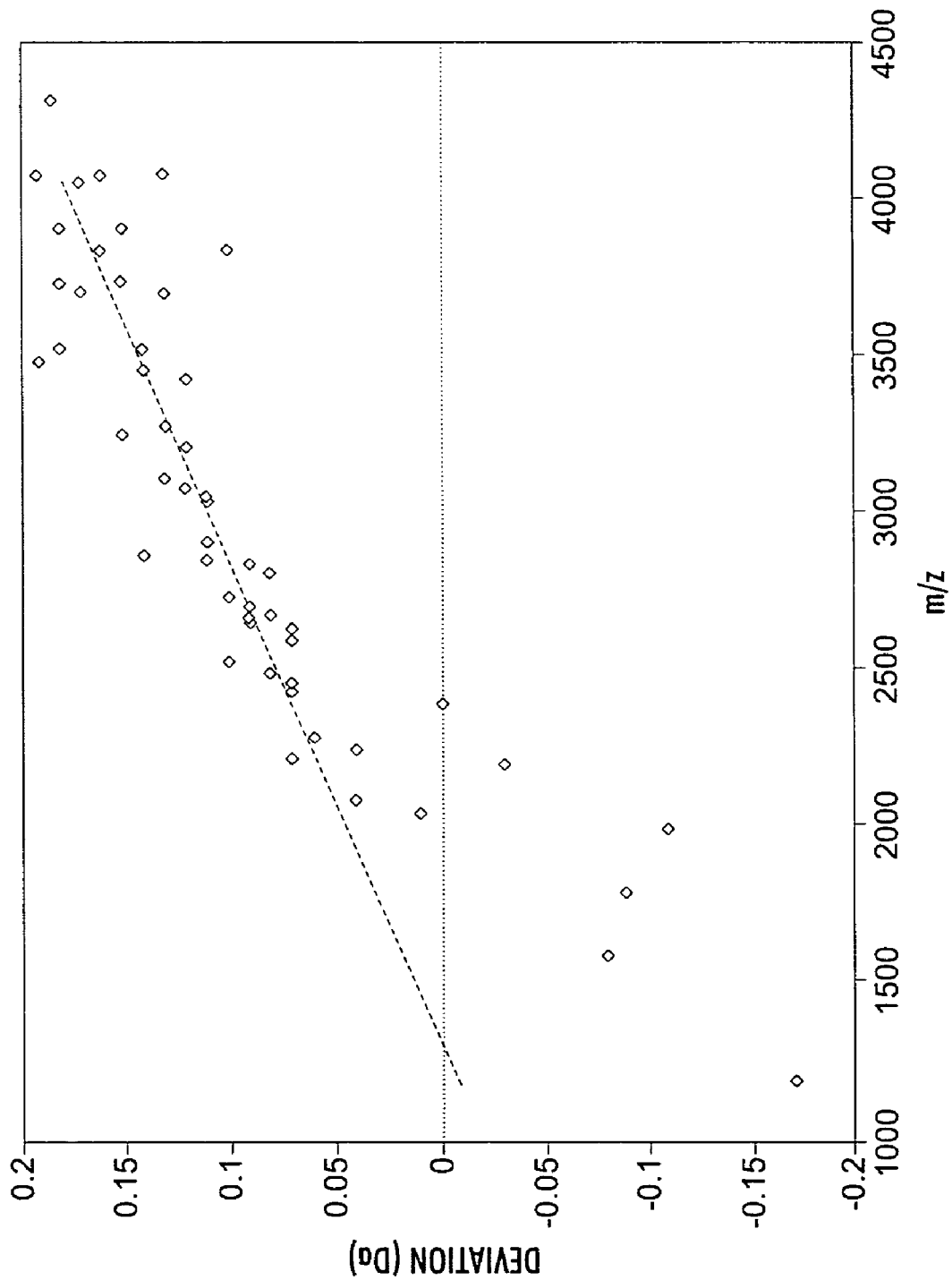
FIGS. 1 and 2 are graphs of two mass spectra taken at different times on the same TOF instrument from the same sample. The two graphs plot deviation (observed mass minus theoretical mass) versus the measured mass of the peak and show how instrument bias can change between spectra.
Figure 2:
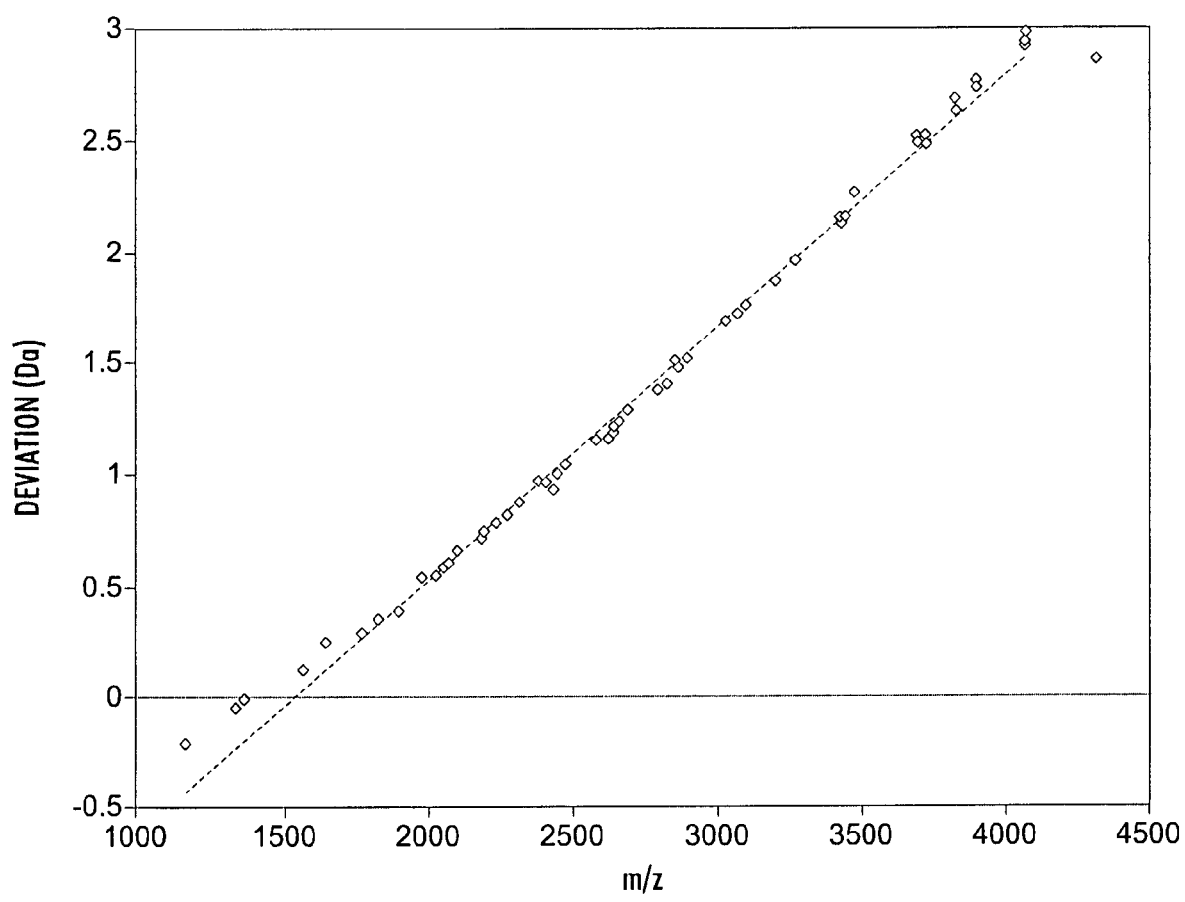

In accordance with the present exemplary embodiment, a new method is provided for recalibrating a mass spectrum of unknown macromolecules or fragments using the peaks of the spectrum itself, thus improving the ability to perform molecular identifications. The term "recalibration" as used herein refers to the correction of measured m/z readings, based upon tentative assignment of specific molecules to spectral peaks and/or differences between peaks, so the measured m/z reading is closer to the "true" value of that m/z reading. The method has been tested on glycan and peptide spectra from TOF, QTOF, and ion-trap instruments from three different laboratories, but is particularly applicable to spectra from time-of-flight mass spectrometers. After recalibration, the precision of a TOF spectrum is typically about 0.03 Da over the entire mass range of 100-4000 Da. The precision of a QTOF spectrum is typically about 0.005 Daltons over the mass range of 100-2000 Da. This precision is significantly better than the 50-100 ppm (that is, 0.1 Da at 1000 Da) typically observed before self-calibration, and even better than the instrument manufacturer's nominal precision of 10 ppm. This improvement translates into greatly reduced error rates for identifications.

A primary strategy of the present exemplary embodiment is the application of robust statistical methods to the recalibration of measured mass spectra. The term "robust" refers to a statistical method wherein changing a single data point by an arbitrary amount does not change the result of an equation or calculation by an arbitrary amount. The advantage of using robust statistical methods in recalibrating mass spectra is that such methods can tolerate a large number of incorrect data points, yet still find the correct result.

Generally, the methods of the exemplary embodiment involve obtaining a mass spectrum of a sample or molecules within that sample. The methods also involve obtaining information concerning the sample, molecules believed to be contained within the sample, or information which can be used to determine the molecules within the sample. Specific examples of such information include, but are not limited to, information about the isotope envelope; information about the molecules, fragments, ions, or constituents thereof within the sample; and information about other molecules, fragments, ions, or constituents thereof. In certain strategies, the information may relate to the distribution of isotopic masses. In certain variations of the exemplary embodiment, candidate identifications are assigned or otherwise made to the mass spectrum using, at least in part, the noted information. From these initial identifications, a data set is prepared. One or more comparisons can be made to generate a data set. A robust statistical method is performed upon the data to generate one or more transformation parameters which are then used in transforming the mass spectrum to provide a recalibrated mass spectrum.

With specific regard to mass spectra, the strategy of the present exemplary embodiment is to find several peaks of observed mass $m_i$ that have known true mass $\underline{m}_i$, and plot $\Delta_i = m_i - \underline{m}_i$ against $m_i$. In the case of OTOF mass spectrometers, the curve is very close to a straight line. If a reasonable estimate is made of the true mass of some of the peaks, then the correct estimates will lie on a smooth curve and known techniques in robust statistics can be utilized to find the curve and distinguish correct estimates (or "on the line") from incorrect estimates (or "outlier"). One such statistical technique is the least median squares method ("LMS"). See Rousseeuw, P J, and Leroy, A M, "Robust Regression and Outlier Detection", John Wiley & Sons, 1987. Practical implementation of LMS uses "Random Sampling Consensus" or RANSAC. More information on RANSAC can be found in Fischler, M A et al., *Communications of the ACM*, 24(6):381-395 (1981), the entire contents of which are incorporated by reference herein. In the case of mass spectra, an affine transformation of the form $y = Ax + B$ is sought, where x is the measured mass and y is the true mass. "Robust Regression and Outlier Detection" states "robust regression . . . tries to devise estimators that are not so strongly affected by outliers. Many people will argue that regression outliers can be discovered by looking a the least square residuals. This is not true. To conclude regression outliers pose a serious threat to standard least squares analysis. Basically, there are two ways out of this problem. The first, and probably most well-known, approach is to construct so-called regression diagnostics. When there is only single outlier, some of these methods work quite well. It is much more difficult to diagnose outliers when there are several of them. The other approach is "robust regression", which tries to devise estimators that are not so strongly affected b outliers. Many statisticians who have vaguely heard of robustness believe that its purpose is to simple ignore the outliers, but this is not true. On the contrary, it is by looking at the residuals from a robust ( or "resistant") regression that outliers a be identified."

An example of a LMS calculation is as follows. A data set P consisting of n points in the plane are identified, some of which lie on a line but many of which do not. The objective is to identify the equation of the line. Multiple subsets $S_j$ are randomly selected from P consisting of k points where k is a small number relative to n and j is the number of subsets, generally a large number. In general, k and j are chosen so that over a sufficiently large number j, a subset $S_j$ will be uncontaminated by outliers and will give a good regression line. Each subset $S_j$ is then given a score by the following method. First, a line is fitted to the k points using the well-known least-squares method. Then for each point in P, the vertical distance between the point and the fitted line is determined; this distance is also known as the residual. The residual for each point in P is squared. The median of the squared residuals is determined and used as the score for that subset $S_j$. The line determined by the subset $S_j$ with the lowest score is taken to represent the "true" line. The estimate of the "true" line is then further refined by classifying each point in P as "on the line" or "outlier" and then re-estimating the equation of the line using only the points previously classified as "on the line."

In the case of peptides, peaks on the mass spectrum are usually difficult to label as belonging to specific sequences of amino acids. Peaks representing single amino acids rarely occur. Combinations of amino acids can also have similar masses. For example, it may be difficult to specify a $b_2$ or $y_2$ ion when amino acid pairs such as PT (198.101 Da) and VV (198.136 Da) have masses within the precision of the instrument. Therefore, the exemplary embodiment uses differences between measured masses rather than the measured masses themselves. The differences are then compared with known "true" masses. For example, if the spectrum includes intense peaks at 400.200, 515.223, and 662.289, it is reasonable to conclude that the first difference (515.223−400.200=115.023) corresponds to the amino acid D (115.027 Da) and the second difference (662.289−515.223=147.066) corresponds to the amino acid F (147.068 Da) even if the specific sequence belonging to the peak at 400.200 cannot be determined. These differences can then be used to estimate the slope A by fitting a line using least-squares to the points (0, 0), (115.023, 115.027), and (262.089, 262.095).

The intercept B can be estimated by using doubly charged ions. For example, if the spectrum includes a peak at 775.402 Da and a peak for a doubly charged ion at 388.200, one can write the equation $A \times 775.402 + B = (A \times 388.200 + B) - 1.0073$ where 1.0073 is the mass of a proton. Combined with the estimate of A, an estimate of B can be obtained. The affine transformation $y = Ax + B$ is then applied to all mass measurements.

In one exemplary embodiment, a robust statistical method, especially LMS, is applied to recalibrate the mass spectrum of a sample glycan. Peaks with a good isotope envelope and small error between predicted and observed masses are identified. LMS is then used to compare the sample mass spectrum with the mass spectrum of a known or theoretical glycan to estimate the slope A, which represents the bias, and then recalibration is performed, and the entire process (including peak identification and recalibration) is iterated. The iteration is important, because it is hard to make peak identifications from a completely uncalibrated time-of-flight spectrum. The difficulty is that the errors grow linearly with mass and become very large for high-mass peaks, so the first iteration will often identify only peaks with small mass, for example, below 1000 Da. After a small number of rounds, the iteration ends and the affine transformation $y = Ax + B$ is applied to all the measured masses of the spectrum.

In another exemplary embodiment, a robust statistical method, especially LMS, is applied to recalibrate the mass spectrum of a sample peptide. The mass spectrum of the sample peptide can be compared against a database of known peptides and their mass spectra is recalibrated using LMS before doing the comparison to determine the best match. Alternatively, in de novo peptide sequencing, LMS can be used to compare the mass spectrum of a sample peptide with the mass spectrum of a theoretical peptide to estimate the slope A.

In another exemplary embodiment, other robust statistical methods such as iterative least squares are used to recalibrate the mass spectrum of a sample macromolecule. In the iterative least squares method, A and B are solved using the least squares method for all points in P. The points with the most error (for example, the worst 20%) are removed and the least squares method is re-iterated.

The analyses, and specifically mass spectra, of a wide array of macromolecules can be recalibrated or otherwise treated according to the exemplary embodiment. For instance, the macromolecule can be a peptide, glycan, or lipid. As used herein, the term "peptide" refers to two or more amino acids linked together chemically. If the number of amino acids is relatively great, the string is sometimes called a polypeptide. More specifically, the macromolecule can be from any class of molecules containing some restrictions on the masses for example peptides are constrained to be composed of a small set of amino acids. As another example polysaccharides are constrained to be composed of a small set of sugars. The macromolecules can also be an amino acid, ionized peptide, ionized polypeptide, ionized amino acid, or a mixture thereof. The macromolecule could also be a sugar, starch, cellulose, monosaccharide, disaccharide, oligosaccharide, ionized glycan, ionized sugar, ionized starch, ionized cellulose, ionized monosaccharide, ionized disaccharide, ionized oligosaccharide, or a mixture thereof. The exemplary embodiment can also be applied to the analysis of non-biological molecules.

Figure 3:
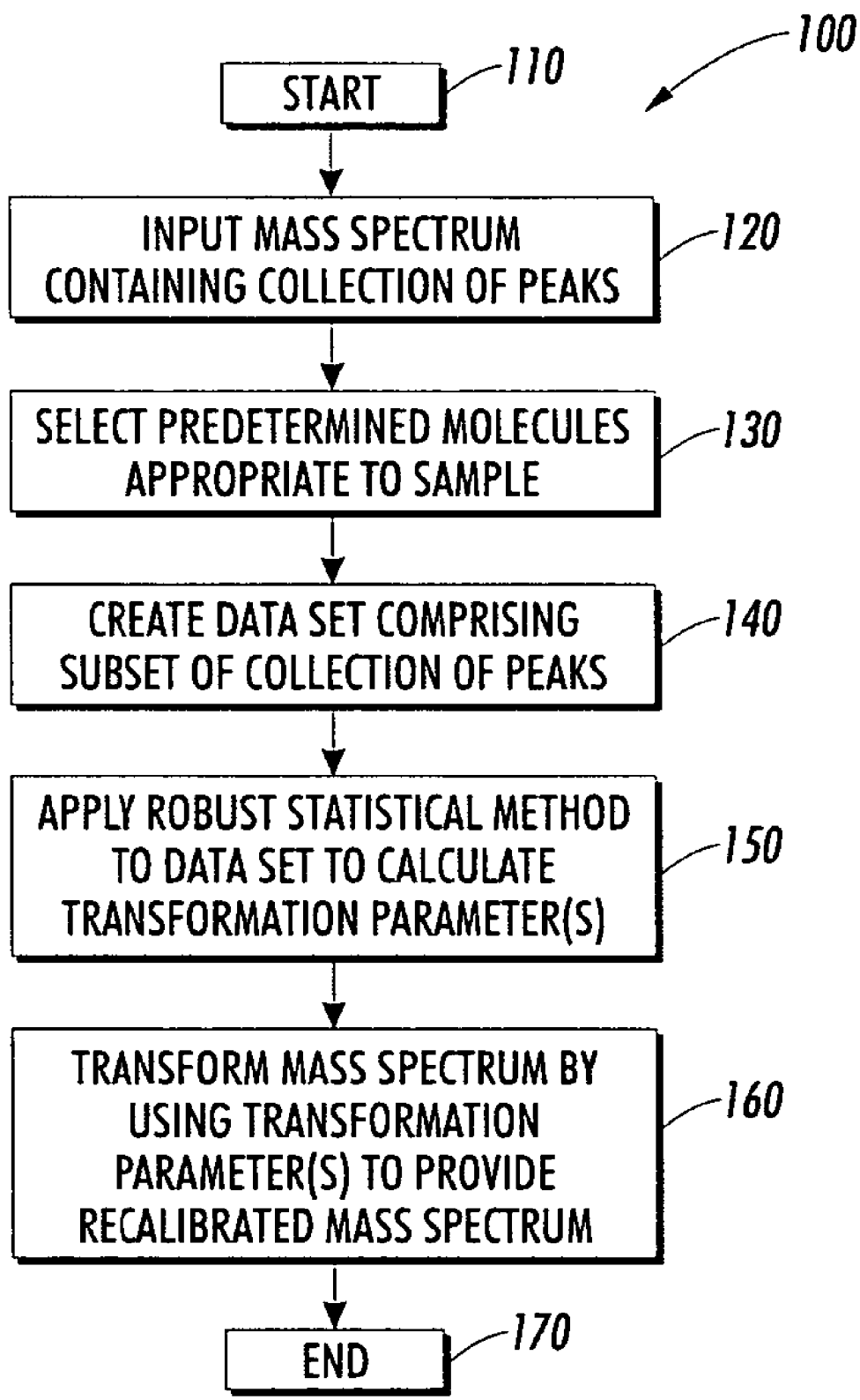
FIGS. 3-7 are schematic flowcharts of various exemplary embodiment recalibration methods.

Specifically, referring to FIG. 3, a method 100 is provided in which a sequence or method is initiated 110. An input mass spectrum containing a collection of peaks is obtained 120. Predetermined molecules appropriate to the sample are selected 130. A data set is created 140 comprising a subset of the collection of peaks from the input mass spectrum. Robust statistical methods are applied 150 to the data set to calculate one or more transformation parameters. The mass spectrum is transformed 160 by using the one or more calculated transformation parameters to provide a recalibrated mass spectrum. The sequence, upon termination by the operator, is stopped 170 or repeated.

Figure 4:
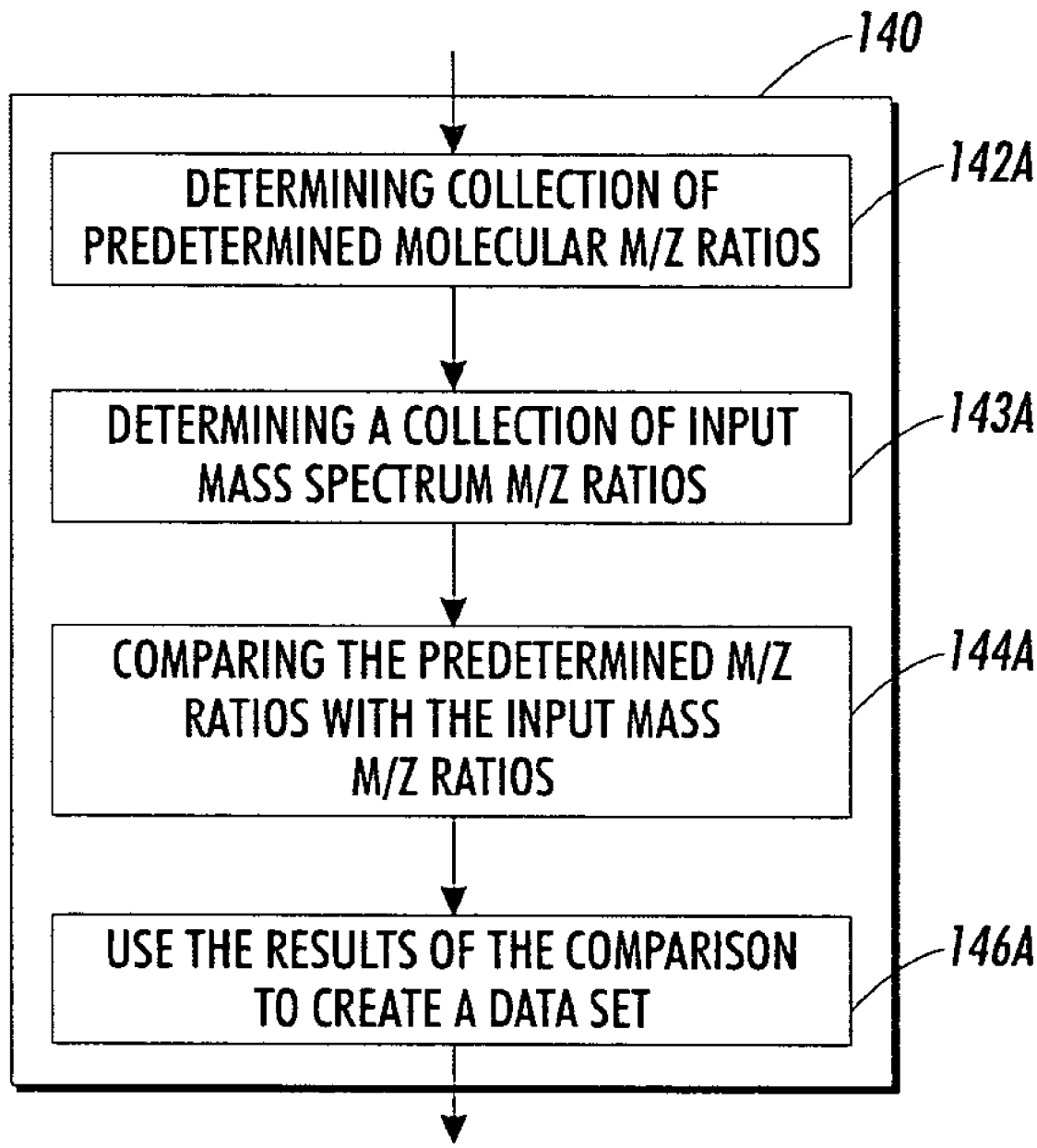

The operation 140 of creating a data set comprising a subset of collection of peaks can, in some alternate embodiments, be conducted as follows. Referring to FIG. 4, a collection of predetermined molecular m/z ratios are determined 142A from the process 130 of FIG. 3. In addition, a collection of input mass spectrum m/z ratios is determined 143A from the mass spectrum. These m/z ratios are compared 144A and the result is used to construct a data set 146A.

Figure 5:
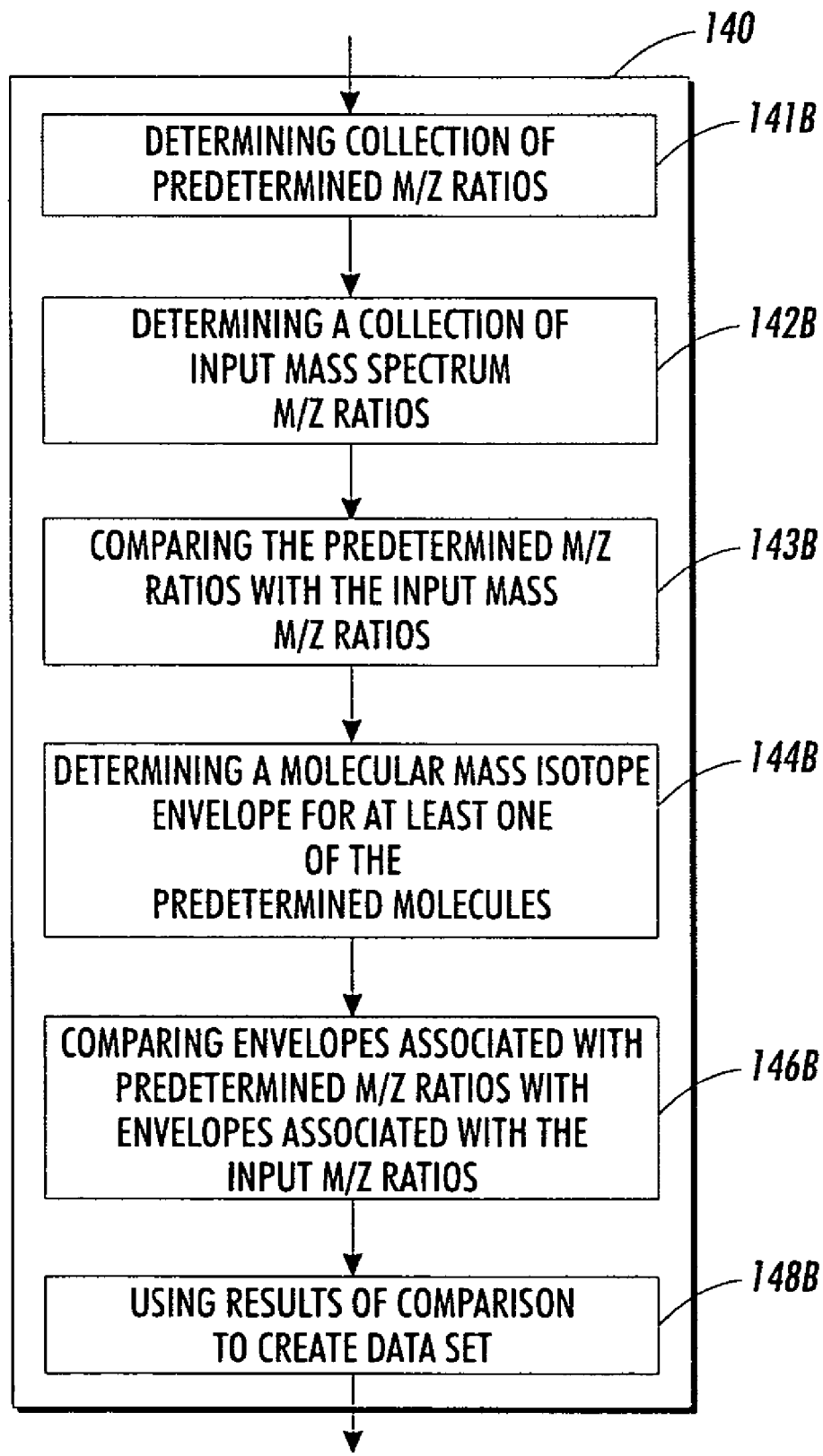

In yet another alternate embodiment shown in FIG. 5, the operation of creating the data set 140 can be performed as follows. A collection of predetermined m/z ratios is determined 141B. A collection of input mass spectrum m/z ratios is determined 142B. Then the predetermined m/z ratios are compared with the input mass m/z ratios 143B. For at least one of the predetermined molecules a molecular mass isotope envelope is determined 144B. Then, the envelopes associated with the predetermined m/z ratios are compared with the envelopes associated with the input mass m/z ratios 146B. At that point the results of the comparison 146B is used to create a data set 148B.

Figure 6:
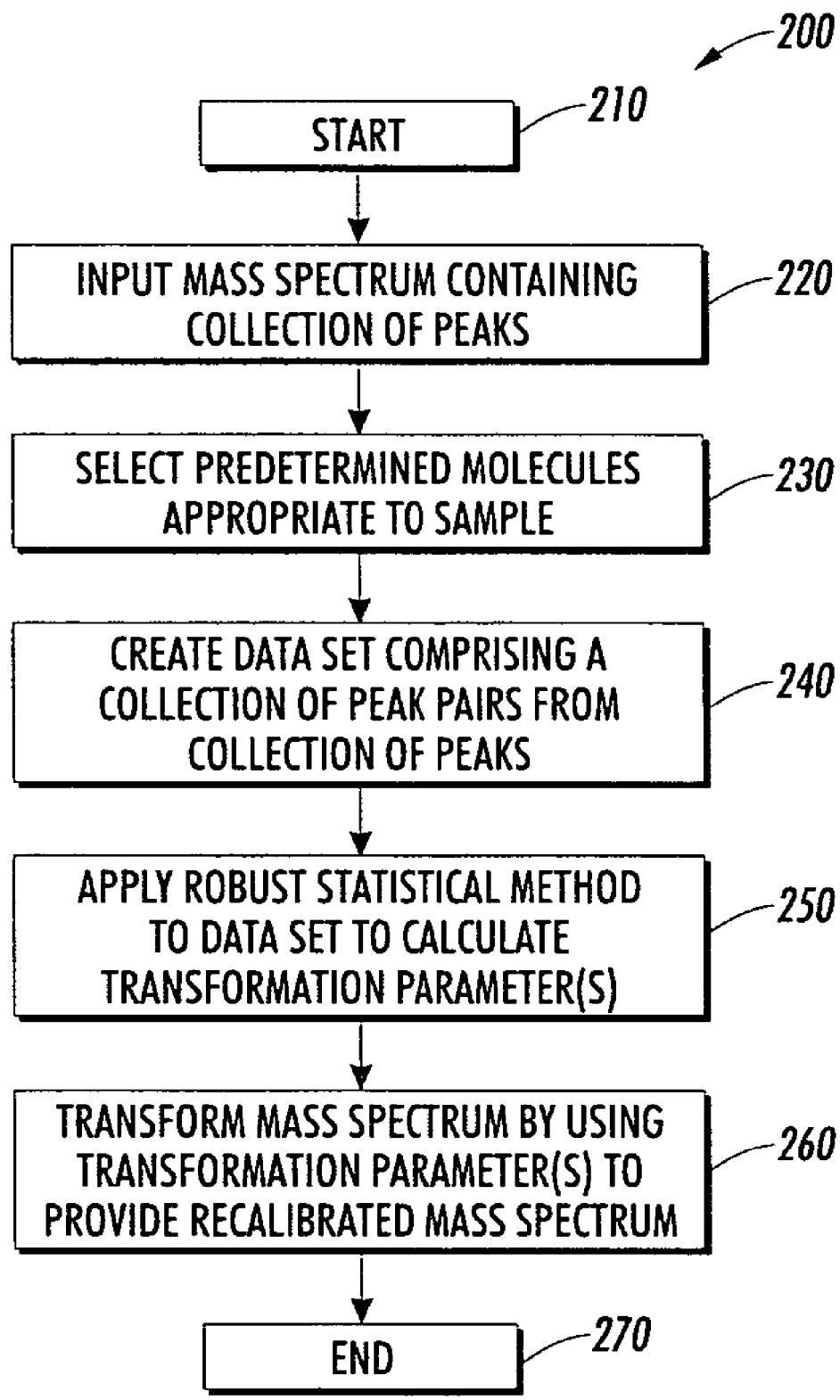

In a variant strategy, an alternate method 200 for recalibration is provided as shown in FIG. 6. A sequence is initiated 210. A mass spectrum containing a collection of peaks is input 220. Predetermined molecules appropriate to the sample are selected 230. A data set is created comprising a collection of peak pairs from the collection of peaks. A robust statistical method is applied 250 to the data set to calculate one or more transformation parameters. A mass spectrum is transformed 260 by using the one or more transformation parameters to provide a recalibrated mass spectrum. The sequence, upon termination by an operator, is stopped 270 or otherwise repeated.

Figure 7:
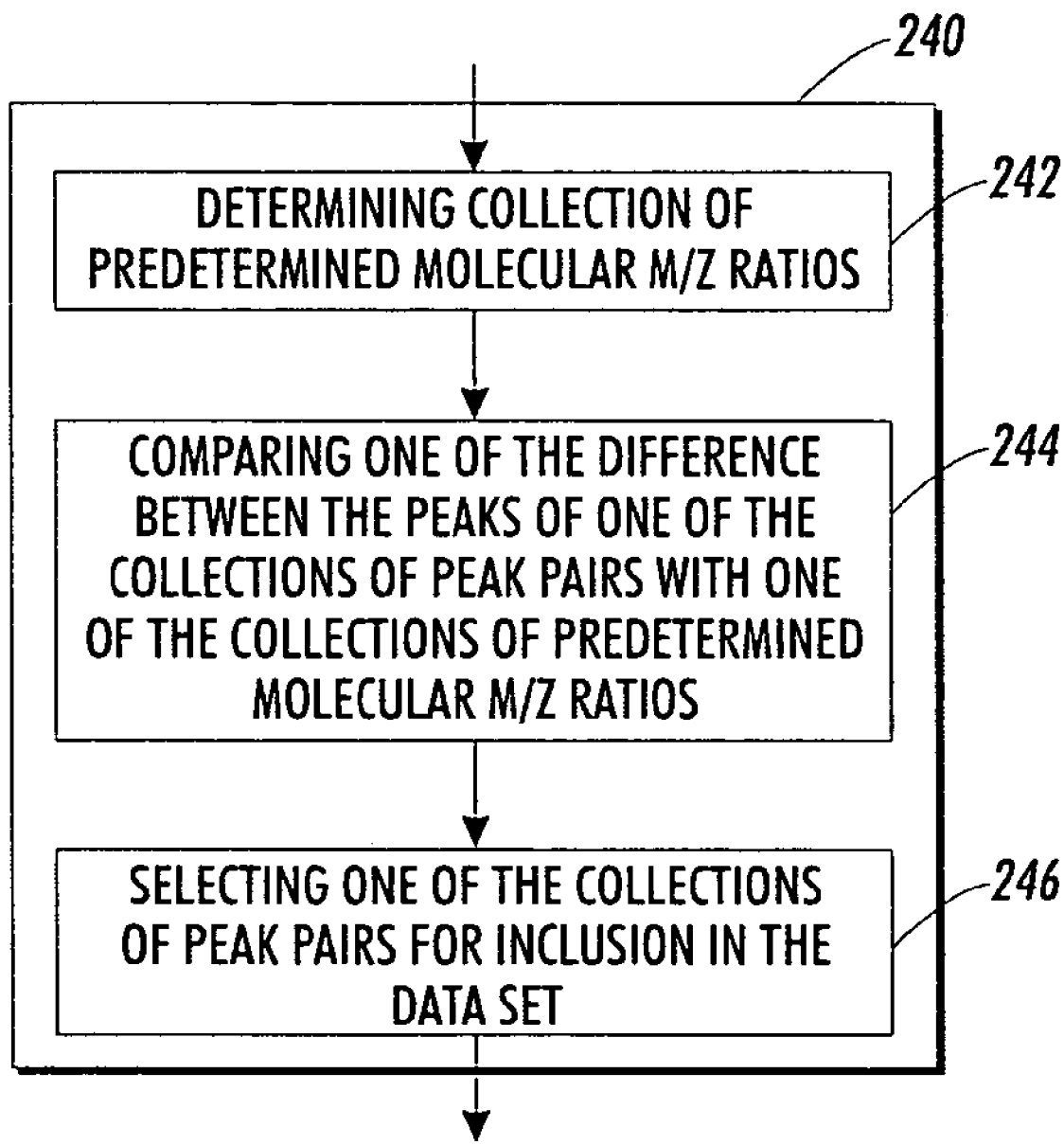

As shown in FIG. 7, the operation 240 of creating the data set can, in some applications, be conducted as follows. A collection of predetermined molecular m/z ratios are determined 242. One of the differences between the peaks of one of the collections of peak pairs is compared 244 with one of the collections of predetermined molecular m/z ratios. One of the collections of peak pairs is selected 246 for inclusion in the data set.

The present exemplary embodiment also relates to systems for performing the methods described herein. The systems generally comprise one or more storage devices for retaining information and data, such as a computer-readable medium, storing mass spectrum data and related information, and a computer program that performs the computational analyses and methods described herein. The systems further comprise a processor, an input device, and an optional output device. The term "computer-readable medium" as used herein includes any type of computer memory or storage device such as but not limited to floppy disks, hard disks, CD-ROMS, Flash ROMS, nonvolatile ROM, and RAM.

Figure 8:
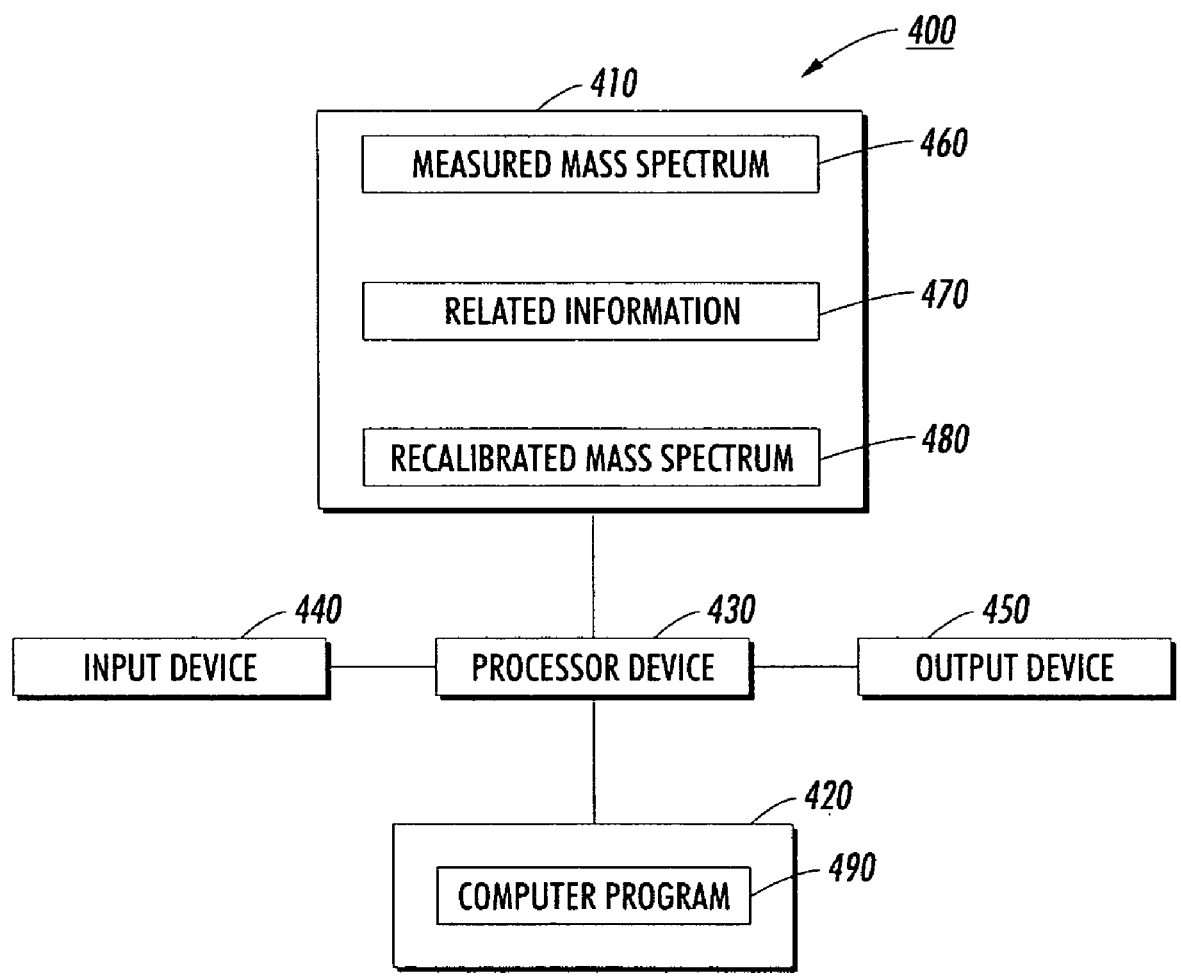
FIG. 8 is a schematic of an exemplary embodiment system.

Specifically, referring to FIG. 8, a system 400 is illustrated including a first storage device 410, a second storage device 420, a processor device 430, an input device 440, and an output device 450. Each device is in communication with the processor device 430 via a wired or wireless communication path, such as a network, serial or parallel port, or any other suitable means of communication. The system 400 provides a recalibrated mass spectrum of a sample, such sample may include one or more macromolecules. The system 400 includes the first storage device 410 which serves to maintain a mass spectrum 460, related information 470 corresponding to the mass spectrum, and the recalibrated mass spectrum 480. The system 400 also includes the second storage device 420 that maintains computer-executable instructions, including a computer program 490 can be programmed in a variety of different configurations. The computer program 490 can be programmed to input and/or retain a mass spectrum that contains a collection of peaks or information indicative of such peaks. The computer program 490 can be further programmed to select predetermined molecules appropriate to the sample. And, the computer program 490 can be additionally programmed to create a data set comprising a subset of the collection of peaks. In another configuration, the computer program 490 can be programmed to input and/or retain a mass spectrum that contains a collection of peaks or information indicative of such peaks. The computer program 490 can be further programmed to select predetermined molecules appropriate to the sample. And, the computer program 490 can be further programmed to create a data set comprising a collection of peak pairs from the collection of peaks. In both configurations, the computer program 490 applies a robust statistical method to the data set to thereby provide at least one transformation parameter. And, the computer program 490 transforms the mass spectrum 460 by using the at least one transformation parameter to thereby provide the recalibrated mass spectrum 480. The output device 450 generally serves to provide a visual illustration or graphical representation of the recalibrated mass spectrum. As will be appreciated, the output device 450 may be a printer device and/or a display device. The output device 450 may also include a communication port through which data, such as the recalibrated mass spectrum 480 may be communicated to other devices.

In the exemplary embodiment, the first and second storage devices 410, 420 are shown as separate devices. However, in other embodiments, the contents of the first and second storage devices 410, 420 may be stored in a common storage device. Alternately, three or more storage devices may be utilized instead of the two shown in FIG. 8. In further embodiments, a portion of the contents of one or more of the first and second storage devices 410, 420 may be embedded in memory associated with the processor device 430.

The input device 440 may include a keyboard, keypad, pointing device, or other types of controls to operate the processor device 430. The input device 440 may also include a measurement device and/or a communication port by which data, such as the mass spectrum 460 and related information 470 may be received.

The processor device 430 may run or otherwise execute the computer program 490 which includes computer-executable instructions for the processor device 430 to read data from the mass spectrum 460 and related information 470, process the data, and store data associated with the recalibrated mass spectrum 480. The computer program may also include computer-executable instructions for the processor device 430 to provide data from the mass spectrum 460, related information 470, and/or recalibrated mass spectrum 480 to a display device and/or printer device associated with the output device 450. The computer program may include computer-executable instructions for the processor device 430 to request data associated with the mass spectrum 460 and/or related information 470 from a measurement device associated with the input device 440 or from another device via a communication port associated with the input device 440. The computer program may include computer-executable instructions for the processor device 430 to send data associated with the mass spectrum 460, related information 470, and/or recalibrated mass spectrum 480 to another device via a communication port associated with the output device 450.

The present exemplary embodiment also relates to computer readable media having computer-executable instructions for performing a method, such as those described herein and schematically depicted in FIGS. 3-7. The method generally involves applying a robust statistical method to a data set which is obtained from comparing mass-to-charge ratios, or comparing peaks or differences between peaks of measured and hypothetical spectra. Applying the robust statistical method thereby provides at least one transformation parameter. The method also involves transforming a mass spectrum by using the at least one transformation parameter to provide a recalibrated mass spectrum.

Specifically, in one version, the exemplary embodiment provides computer-readable media having computer executable instructions for performing a method which comprises obtaining a mass spectrum of a plurality of macromolecules. The mass spectrum contains a plurality of peaks each of which corresponds to a mass-to-charge ratio. The method also comprises selecting a plurality of predetermined molecules appropriate to the sample. The method additionally comprises creating a data set comprising a subset of the plurality of peaks wherein each of the subset of the plurality of peaks is assigned to one or more of the plurality of predetermined molecules. The method also comprises applying a robust statistical method to the data set to calculate at least one transformation parameter. And, the method comprises transforming the mass spectrum by using the at least one transformation parameter to thereby provide the recalibrated mass spectrum.

In another aspect, the computer-readable media includes computer-executable instructions for performing a method comprising obtaining a mass spectrum of a plurality of macromolecules. The mass spectrum contains a plurality of peaks each of which corresponds to a mass-to-charge ratio. The method also comprises selecting a plurality of predetermined molecules appropriate to the sample. And, the method comprises creating a data set comprising a plurality of peak pairs from the plurality of peaks wherein each of the peak pairs is assigned to one of the plurality of predetermined molecules. The method also comprises applying a robust statistical method to the data set to calculate at least one transformation parameter. And, the method comprises transforming the mass spectrum by using the at least one transformation parameter to thereby provide a recalibrated mass spectrum.

EXAMPLES

Recalibration of Glycan Mass Spectra

Over 100 mass spectra of N-glycans from mouse kidney were obtained. N-glycans were released from a kidney peptide extract by peptide:N-glycanase (PNGase F) treatment and were subsequently permethylated before analysis by mass spectrometry, using MALDI-TOF mass spectrometry in the strategy described by Sutton-Smith, M. et al., *Tetrahedon: Asymmetry*, 11(2):363-369 (2000), which is incorporated by reference herein. Permethylation was performed using the sodium hydroxide procedure as described by Dell, A. et al. in *Cell Biology: A Laboratory Handbook*, Vol. 4, J. E. Celis, Ed. (Academic Press, San Diego, in press), which is incorporated by reference herein. MALDI data were acquired using an ABI Perspective Biosystems Voyager-DE™ sSTR mass spectrometer in the reflectron mode with delayed extraction. Permethylated samples were dissolved in 10 µl of methanol, and 1 µl of dissolved sample was premixed with 1 µl of matrix (2,5-dihydrobenzoic acid, Sigma-Aldrich, UK) before loading onto a 100-well stainless steel sample plate.

The mass spectrum was recalibrated by first finding about 15 high-confidence peak assignments. These high-confidence peaks were relatively high-intensity peaks (typically among the highest 200 peaks), had isotope envelopes that closely matched the theoretical value of the potential matching glycan assigned to it, and had a measured mass very close to the theoretical mass of the potential matching glycan assigned to it (within 100 ppm). For each measured peak $m_i$, the deviation between the measured and theoretical mass was computed $d_i = m_i - $(theoretical mass). The RANSAC algorithm was successively applied to fit the pairs $(m_i, d_i)$ to a line $y = Ax + B$ and determine which of the peaks were high-confidence peaks. For a peak of measured mass m, the correction deviation d' was the difference between the theoretical mass based on the line and the measured mass, $d' = (Am + B) - m$.

Figure 9:
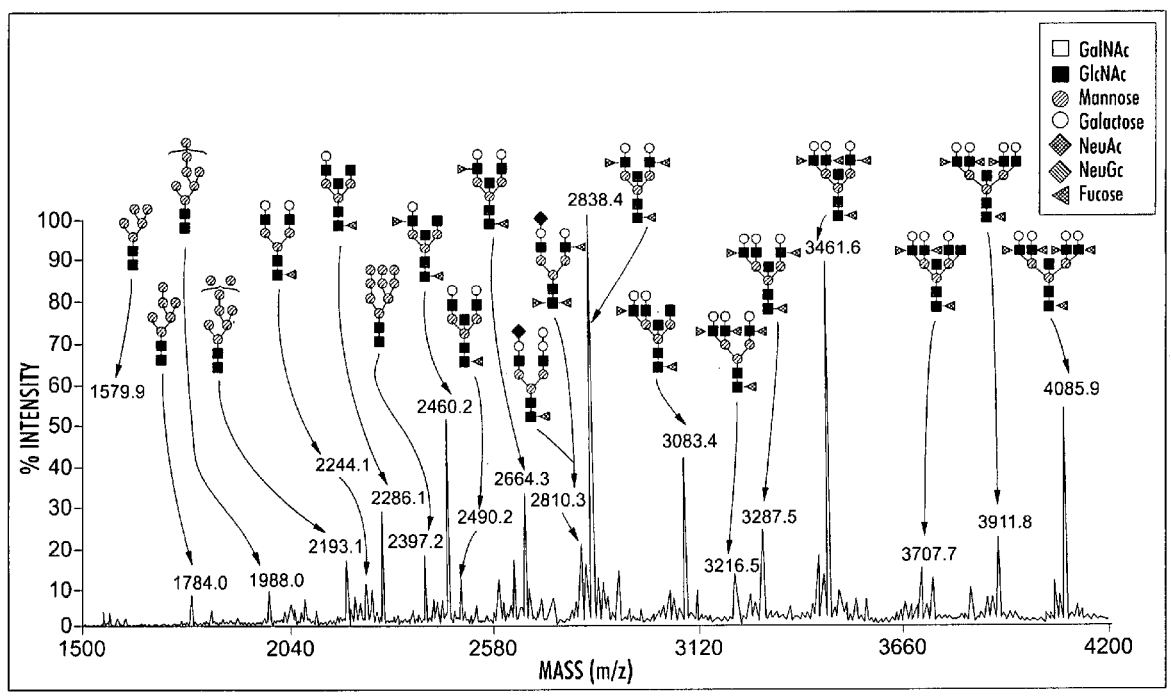
FIG. 9 is a manual annotation of mouse kidney spectrum by a human expert assigning a glycan to each peak.
Figure 10:
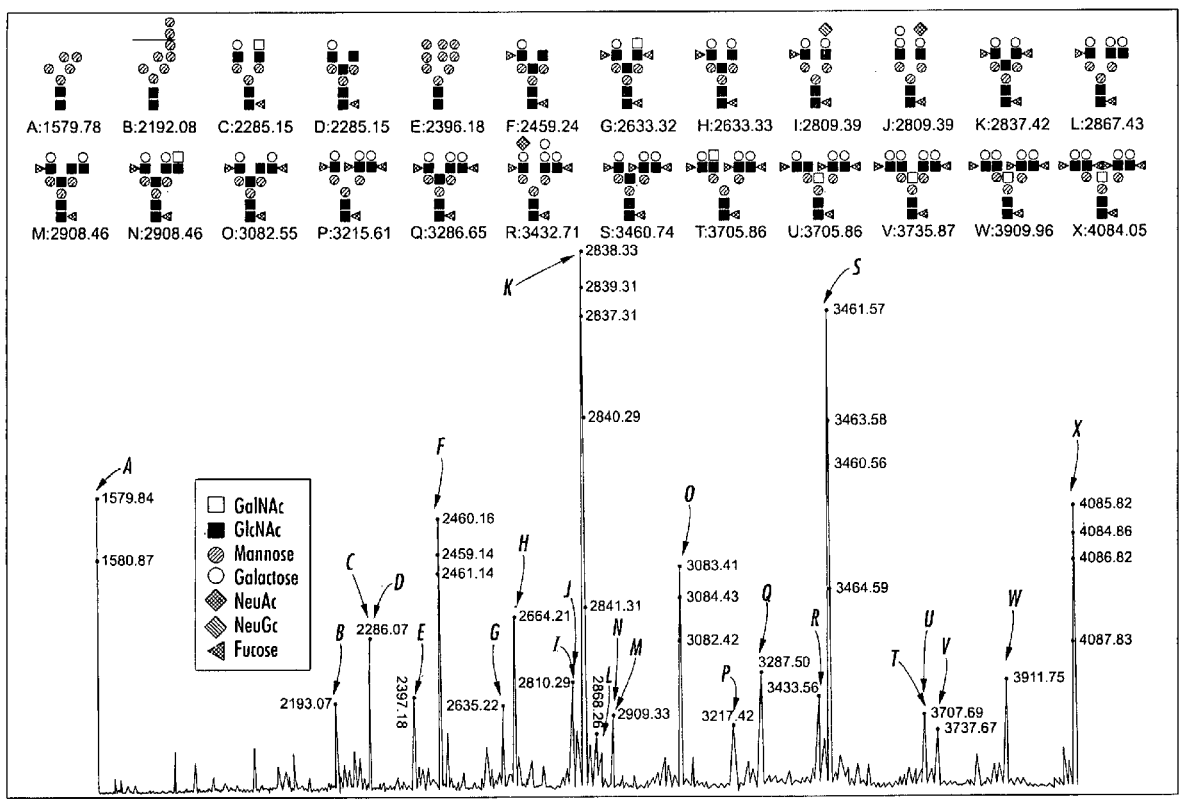
FIG. 10 is an automatic annotation of mouse kidney spectrum using the RANSAC algorithm to assign a glycan to each peak.

The assignment of glycans to mass spectrum peaks made using the RANSAC algorithm were compared to assignments made by human experts, as is currently done. In all cases, the algorithm provided meaningful assignment of probable compositions and structures of glycans to observed peaks in the mass spectrum. One example is given by comparing FIG. 9, which is a mass spectrum hand-annotated by a human expert, with FIG. 10, which is the same mass spectrum automatically annotated using the RANSAC algorithm. Fifteen of the hand-annotated peaks were also identified by the RANSAC algorithm. For twelve of the fifteen the annotations were identical; for the other three the RANSAC algorithm offered two possible structures, one of which matched the hand-annotated one (for the peak at 2810.3 with two alternate expert annotations, the RANSAC algorithm found both). The remaining differences were due to variations in the set of peaks chosen for annotation. The RANSAC algorithm selected peaks for annotation starting with the most intense peak and continuing systematically to the second most intense, etc, whereas the human annotators deviated slightly from this procedure

Recalibration of Peptide Mass Spectra

The RANSAC algorithm was applied to three different sets of peptide mass spectra. The first set consisted of 74 QTOF spectra of tryptic peptides, lengths 7-15, from common reference proteins such as bovine serum albumin, measured on a Micromass Q-TOF II spectrometer. The second set consisted of 106 Q-TOF spectra of tryptic peptides, lengths 6-23, from mouse zona pellucida proteins, and was obtained from the Dell Laboratory (Imperial College, London). These spectra were identified by database search against a large "decoy" database of all mouse proteins without regard for cleavage specificity. The third set consisted of 101 ion-trap spectra of peptides (not necessarily tryptic), lengths 5-14, from common reference proteins, measured on a ThermoFinnegan LCQ-Deca spectrometer, and identified by database search (SEQUEST) against the NCBI nonredundant protein database. These ion-trap spectra were obtained from the Yates Laboratory (The Scripps Research Institute).

The RANSAC algorithm was modified from the description previously given. In particular, the algorithm was modified to discard points that had a residual greater than either 2.5 times the score of the subset $S_j$ determined to represent the "true" line or a user-supplied number corresponding to an estimate of the machine's theoretical mass accuracy. This modification prevented the algorithm from being too aggressive in removing outliers. Based on the observation that intense peaks tend to be more accurate than small peaks, the basic algorithm was also modified to use a weighted least-squares method rather than a least-squares method to refine and re-estimate the line from the set of points classified as "on the line." The weight of a data point p was 1(3+Rank(p)) where Rank(p) was equal to the rank of p in the list of calibration peaks (1 for the most intense peak, 2 for the second most intense, and so forth). Based on the observation that plots of TOF errors have slightly sigmoidal shapes, the basic algorithm was also modified to fit a cubic curve instead of a line if the number of points in P was sufficiently large (14 or more data points).

The RANSAC algorithm was applied in the following manner. For each ladder i, an estimated slope $A_i$ was calculated by dividing the presumed true difference between the first and last peaks of the ladder by their measured difference. The weight of estimate $A_i$ was set to $$MDiff \Big/ \left( \sum_p \text{Rank}(p) \right)$$

for ladders of length 2 and $$4 \times MDiff \Big/ \left( \sum_p \text{Rank}(p) \right)$$

for ladders of length 3, where MDiff denotes the measured mass difference between the first and last peaks in the ladder and the sum in the denominator was over the peaks p in the ladder. The final estimate of the slope A was determined as a weighted trimmed mean of the individual estimates $A_i$ where the top 20% and bottom 20% of the estimates were dropped and the weighted average was formed from the remaining estimates.

The results for a priori recalibration were determined by a posteriori analysis that identified peaks and are listed in Table 1 below.

TABLE 1

Results for a priori recalibration.

| | Med $err_U$ | Med $err_C$ | Med $|err_C|$ | Med $\sigma_U$ | Med $\sigma_C$ | Max $\sigma_U$ | Max $\sigma_C$ |
|---|---|---|---|---|---|---|---|
| QTOF | .0402 | .0003 | .0089 | .0220 | .0072 | .0502 | .0241 |
| TOF | .0843 | .0271 | .0277 | .0462 | .0286 | .0965 | .0678 |

Here err denotes the mean mass error (true mass minus measured mass) and σ denotes the standard deviation of mass errors for b- and y-ion peaks in a spectrum. Subscripts denote Uncalibrated and Calibrated, and Med and max denote the median and maximum over spectra. Thus Med $err_u$ is the median (over spectra) of the mean (over peaks) of the uncalibrated mass errors. For comparison, cubic a posteriori recalibration gives Med $\sigma_c$=0.0034 for QTOF and Med σhd c=0.0251 for TOF. All units are Da.

The most important metric of algorithm performance is the standard deviation of mass errors after recalibration, Med σ, because a constant offset in the mass measurements (which would increase the median error but not the standard deviation) cannot be corrected by slope A alone. The results can be interpreted by considering that before recalibration the "typical" QTOF spectrum had an offset of 0.0402 (true mass minus measured mass; i.e., measured masses tend to be low) and a typical peak had an additional error 0.0220 in either direction. After recalibration the spectrum had an offset of 0.0089 Da in either direction and a typical peak has an additional error of 0.0072 in either direction. After recalibration the typical TOF spectrum had an offset of 0.0277 and a typical peak had an additional error of 0.0286. The standard deviation of mass errors dropped significantly as reflected by the differences in Med $\sigma_u$ and Med $\sigma_c$. The algorithm never increased the standard deviation of the mass errors, but for three of the QTOF spectra and 21 of the TOF spectra, the standard deviation decreased by less than 20%.

Estimating the intercept B was performed using doubly charged peaks as described above. However, only about half of the spectra, both QTOF and TOF, had identifiable doubly-charged peaks and even the spectra with such peaks could not be recalibrated to significantly greater accuracy than was achieved using slope alone. For example, Med $\sigma_c$ for QTOF improved from 0.0072 to 0.0058, but Med $\sigma_c$ for TOF changed only from 0.0286 to 0.0284. For de novo sequencing, B is less important than A because B does not affect the relative locations of peaks, for example the differences between successive y-ions, but only their absolute locations.

The mass of the parent ion was also recalibrated. An accurate determination of the parent mass aids in eliminating candidates when database lookup methods are used and aids in placing b- and y-ion peaks on a common scale in de novo sequencing. The mass of the parent ion had already been measured in the first round of tandem MS, but its accuracy could be improved using recalibration. Each pair of eligible peaks p and q whose m/z measurements summed to within a user-supplied tolerance of the parent mass (0.2 Da for QTOF and 0.3 Da for TOF) plus a proton gives an estimate of the total mass. The mass of the parent ion was recalibrated as the weighted averages of the complementary pairs where the average of each pair was weighted as 1/(Rank(p)+Rank(q)). In the rare case that there were no complementary pairs, the mass of the parent ion was not changed. A trimmed mean was not used because typically there are only a few complementary pairs within a mass spectrum. For QTOF, the median error improved from 0.0982 to 0.0045; the worst error improved from 0.1968 to 0.0918. On only one of the 74 spectra did the error get worse with recalibration, changing from 0.0619 to 0.0880. For TOF, the median error improved from 0.1902 to 0.0614, and the worst error improved from 0.4594 to 0.3272. On six of the 106 spectra the error got worse, with the worst change from 0.1185 to 0.1640.

Overall, a priori recalibration was very successful, especially for TOF spectra for which it achieved only slightly worse performance than a posteriori recalibration. The difference between the QTOF and TOF errors resulted from the difference in measurement errors. For TOF, measurement errors are about equal to the intercept B and hence lack of data for estimating B is not a major problem. In contrast, QTOF measurement errors are smaller than B by a factor of about 4 and hence a regression model with B could only achieve partial success.

For a posteriori recalibration, it was assumed that the amino acid sequence of the peptide was known. This might occur when using a database to look up candidate sequences for comparison against the mass spectrum of the unknown spectrum; each candidate sequence is in turn considered to be the correct sequence. The correct sequence recalibrates the mass spectrum well, so that a large number of peaks correspond to predicted ions. In contrast, an incorrect sequence recalibrates the spectrum less well and fewer peaks correspond to ions. This correctness is reflected in the score assigned to each candidate sequence.

For a posteriori recalibration, eligible peaks were chosen by a different method than for a priori recalibration. The preprocessing step allowed more lower-intensity peaks through (with Rank up to 15 times the number of amino acids) and also allowed peaks that matched a-ions and water losses in addition to b- and y-ions. Initially, a data point was defined for each predicted peak that matched an observed peak within a user-supplied relative tolerance (150 ppm for QTOF and 250 ppm for TOF). The RANSAC algorithm was used to fit a regression line to these points. A second round of recalibration was then performed, this time with a user-supplied absolute tolerance (0.025 Da for QTOF, 0.10 Da for TOF) for peak identification. The RANSAC algorithm was used to fit either a line or a cubic curve to the new set of points as selected by the user. If the number of points was fewer than 14, the algorithm would only fit a line, even if the "cubic" option was selected.

The results for a posteriori recalibration are listed in Table 2 below.

TABLE 2

Results for a posteriori recalibration.

| | Med $err_U$ | Med $err_C$ | Med $|err_C|$ | Med $\sigma_U$ | Med $\sigma_C$ | Max $\sigma_U$ | Max $\sigma_C$ |
|---|---|---|---|---|---|---|---|
| Linear | | | | | | | |
| QTOF | .0373 | −.00003 | .0006 | .0239 | .0034 | .0402 | .0062 |
| TOF | .0682 | .0018 | .0047 | .0551 | .0264 | .0947 | .0484 |
| Ion Trap | .0663 | −.0008 | .0167 | .1010 | .0996 | .1920 | .1662 |
| Cubic | | | | | | | |
| QTOF | .0373 | −.0001 | .0008 | .0239 | .0034 | .0402 | .0058 |
| TOF | .0682 | −.0012 | .0046 | .0551 | .0251 | .0947 | .0487 |

Here err denotes the mean mass error (true mass minus measured mass) and a denotes the standard deviation of mass errors for a-, b-, and y-ion peaks, and water losses thereof. The "Linear" fit always used a regression line; the "Cubic" fit used a cubic curve if the number of points was at least 14 and a line otherwise. Most spectra qualified for the cubic curve; 49 out of 74 QTOF spectra and 91 out of 106 TOF spectra. All units are Da.

As shown, a cubic curve performed only slightly better than a linear regression. By comparison, ordinary un-weighted least-squares line fitting gave significantly worse results. For the 74 QTOF spectra, one round of least-squares, where a line was fit to all peaks within 150 ppm of predicted peaks, gave Med $\sigma C=0.0106$ and Max $\sigma C=0.0366$, compared to 0.0034 and 0.0058 with the two-round RANSAC algorithm used. Two rounds of ordinary least-squares, using thresholds of 150 ppm and 0.025 Da, did substantially better than one round, achieving Med $\sigma C=0.0039$ and Max $\sigma C=0.0076$.

Worse results in recalibration also translated into worse results in de novo sequencing. The 74 QTOF spectra were scored against likely decoys (200-1000 decoys each) such as sequences with transposed letters and close-mass substitutions such as K for Q and DY for MF. The scoring weighted identified peaks by their proximity to the predicted mass and by some a priori probability of observing such a peak (so that central y-ions have high weights). No recalibration at all gave 22.5 correct answers where a correct answer meant the highest scoring sequence was indeed the true sequence. 5 spectra for which the true sequence tied for first with one other sequence were counted as one-half correct answer each. Ordinary least-squares gave 39 correct answers; two-round least-squares gave 54 correct answers; the two-round RANSAC algorithm gave 62 correct answers. The best results—65 correct answers—were obtained by the two-round RANSAC algorithm without the cubic option. Scoring performance appeared to depend sensitively on recalibration; a small difference between two-round least squares and the linear RANSAC algorithm in Med $\sigma C$ (0.0039 to 0.0034) became a significant difference in scoring (20 errors to 9 errors).

Figure 11:
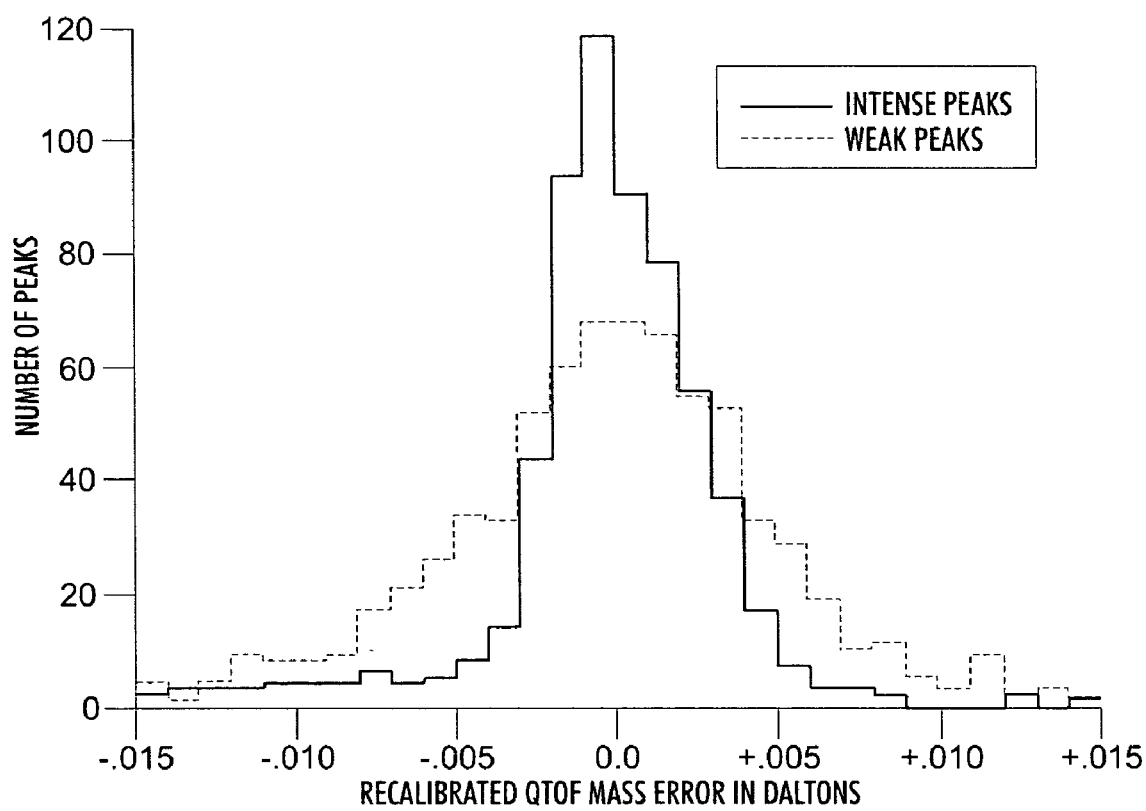
FIG. 11 is a histogram showing the mass errors of peaks in all 74 QTOF spectra after a posteriori recalibration. It shows that intense peaks are measured more accurately than weak peaks.

FIG. 11 is a histogram showing the mass errors of peaks in all 74 QTOF spectra after a posteriori re-calibration. It shows that intense peaks (those with Rank from 1 to 20) were measured more accurately than weak peaks (Rank>20).

A posteriori recalibration was also performed on ion-trap data. Absolute tolerances were used in both the first and second rounds of peak identification (0.40 Da and 0.35 Da respectively) because ion traps do not have structured errors. The results are included in Table 2. The uncalibrated ion-trap spectra did have a small constant offset that could be corrected, reflected in the fact that Med errU=0.0663 improved to Med|errC|=0.0167. However, the standard deviation of errors could not be significantly improved, reflected in the fact that Med $\sigma U=0.1010$ is insignificantly larger than Med $\sigma C=0.0996$. The worst ion-trap spectra did have slight linear trends in their errors, reflected in the fact that Max $\sigma U=0.1920$ improved to Med $\sigma C =0.1662$.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A method for providing a recalibrated mass spectrum of a sample including a plurality of macromolecules, said method comprising:
   obtaining a mass spectrum of said plurality of macromolecules from a mass spectrometer, said mass spectrum containing a plurality of peaks each of said plurality of peaks corresponding to a mass-to-charge ratio;
   selecting a plurality of predetermined molecules appropriate to said sample by a computer processor operating a particularly configured computer program;
   creating a data set comprising a subset of said plurality of peaks by a computer processor operating a particularly configured computer program, wherein each peak of said subset of said plurality of peaks is assigned to one or more of said plurality of predetermined molecules;
   applying a robust statistical method to said data set to calculate at least one transformation parameter by a computer processor operating a particularly configured computer program,
   the robust statistical method involving the statistical method distinguishing correct estimates from incorrect estimates of data points wherein changing a single data point by an arbitrary amount does not change the result of an associated equation or calculation by an arbitrary amount resulting in tolerance of a large number of incorrect data points;
   transforming, by self-calibration, said obtained mass spectrum by using said at least one transformation parameter to provide said recalibrated mass spectrum by a computer processor operating a particularly configured computer program;
   displaying or storing said recalibrated mass spectrum on an output device.

2. The method of claim 1, wherein said plurality of macromolecules is selected from one or more of the group consisting of a peptide, a polysaccharide, a glycan, and a glycopeptide.

3. The method of claim 1, wherein the step of creating said data set further comprises:
   determining a plurality of predetermined molecular mass-to-charge ratios, wherein each of said plurality of predetermined molecular mass-to-charge ratios is determined from one of said plurality of predetermined molecules;
   comparing one of said plurality of peaks with one of said plurality of predetermined molecular mass-to-charge ratios; and
   selecting, responsive to the step of comparing, said one of said plurality of peaks for inclusion in said data set.

4. The method of claim 1, wherein the step of creating said data set further comprises:
   determining a plurality of predetermined molecular mass-to-charge ratios, wherein each of said plurality of predetermined molecular mass-to-charge ratios is determined from one of said plurality of predetermined molecules;
   comparing one of said plurality of peaks with one of said plurality of predetermined molecular mass-to-charge ratios, said one of said plurality of predetermined molecular mass-to-charge ratios associated with one of said plurality of predetermined molecules;
   determining a molecular mass isotope envelope for said one of said plurality of predetermined molecules;
   comparing a peak isotope envelope associated with said one of said plurality of peaks with said molecular mass isotope envelope; and selecting, responsive to the step of comparing one of said plurality of peaks and the step of comparing a peak isotope envelope, said one of said plurality of peaks for inclusion in said data set.

5. The method of claim 1, wherein the step of applying a robust statistical method is performed by applying least median square (LMS).

6. The method of claim 1, wherein the step of applying a robust statistical method is performed by applying iterative least squares.

7. The method of claim 1, wherein the step of applying a robust statistical method provides at least one linear transformation parameter and the step of transforming said mass spectrum is performed by linearly transforming said mass spectrum by use of said at least one linear transformation parameter.

8. The method of claim 1, wherein the step of applying a robust statistical method provides at least one polynomial transformation parameter and the step of transforming said mass spectrum is performed by transforming said mass spectrum according to a polynomial transformation and using said at least one polynomial transformation parameter.

9. The method of claim 1, wherein said plurality of macromolecules comprises at least one peptide, said peptide having a tentative identification and wherein said plurality of predetermined molecules comprises at least one peptide fragment of said tentative identification.

10. The method of claim 1, wherein said plurality of macromolecules comprises at least one glycan and said plurality of predetermined molecules comprises at least one predetermined glycan.

11. The method according to claim 1, wherein the self-calibration of the mass spectrum includes the obtaining, selecting, creating, applying and transforming steps.

12. The method according to claim 1, wherein when the recalibrated mass spectrum is a Time of Flight (TOF) recalibrated spectrum generated by a Time of Flight Spectrometer, the TOF recalibrated spectrum having a precision of about 0.03 Da over a mass range of 100-4000 Da.

13. The method according to claim 1, wherein when the recalibrated mass spectrum is a Quadrupole time of Flight (QTOF) recalibrated spectrum generated by a Quadrupole Time of Flight spectrometer the QTOF recalibrated spectrum having a precision of about 0.005 Da over a mass range of 100-2000 Da.

14. The method of claim 1, wherein the transformation is defined as an affine transformation of the form y=Ax+B, where x is the measured mass and y is the true mass.

15. A method for providing a recalibrated mass spectrum of a sample including a plurality of macromolecules, said method comprising:
obtaining a mass spectrum of said plurality of macromolecules from a mass spectrometer, said mass spectrum containing a plurality of peaks each of said plurality of peaks of the obtained mass spectrum corresponding to a mass-to-charge ratio;
selecting a plurality of predetermined molecules appropriate to said sample by a computer processor operating a particularly configured computer program;
creating a data set comprising a plurality of peak pairs from said plurality of peaks by a computer processor operating a particularly configured computer program, wherein each of said peak pairs is assigned to one of said plurality of predetermined molecules, and wherein the step of creating said data set by the particularly programmed computer program running the computer processor further comprises:
determining a plurality of predetermined molecular mass-to-charge ratios, wherein each of said plurality of predetermined molecular mass-to-charge ratios is determined from one of said plurality of predetermined molecules;
comparing one of said difference between the peaks of one of said plurality of peak pairs with one of said plurality of predetermined molecular mass-to-charge ratios; and
selecting, responsive to the step of comparing, said one of said plurality of peak pairs for inclusion in said data set,
applying a robust statistical method to said data set to calculate at least one transformation parameter, wherein the step of applying a robust statistical method is performed by applying least median square (LMS),
transforming, by self-calibration, said obtained mass spectrum by using said at least one transformation parameter to provide said recalibrated mass spectrum by a computer processor operating a particularly configured computer program,
the robust statistical method involving the statistical method distinguishing correct estimates from incorrect estimates of data points wherein changing a single data point by an arbitrary amount does not change the result of an associated equation or calculation by an arbitrary amount resulting in tolerance of a large number of incorrect data points;
displaying or storing said recalibrated mass spectrum on an output display device; and
wherein when the recalibrated mass spectrum is a Quadrupole time of Flight (QTOF) recalibrated spectrum generated by a Quadrupole Time of Flight spectrometer the QTOF recalibrated spectrum having a precision of about 0.005 Da over a mass range of 100-2000 Da.

16. The method of claim 15, wherein said plurality of macromolecules comprises at least one peptide and said plurality of predetermined molecules comprises at least one amino acid residue.

17. The method of claim 15, wherein said plurality of macromolecules comprises at least one glycopeptide and said plurality of predetermined molecules comprises at least one amino acid residue or at least one monosaccharide.

18. The method of claim 15, wherein the step of applying a robust statistical method is performed by applying iterative least squares.

19. The method of claim 15, wherein the step of applying a robust statistical method provides at least one linear transformation parameter and the step of transforming said mass spectrum is performed by linearly transforming said mass spectrum by use of said at least one linear transformation parameter.

20. The method of claim 15, wherein the step of applying a robust statistical method provides at least one polynomial transformation parameter and the step of transforming said mass spectrum is performed by transforming said mass spectrum according to a polynomial transformation and using said at least one polynomial transformation parameter.

21. The method of claim 15, wherein the transformation is defined as an affine transformation of the form y=Ax+B, where x is the measured mass and y is the true mass.

22. A system for providing a recalibrated mass spectrum of a sample including a plurality of macromolecules, the system comprising:
a first storage device operative to maintain a mass spectrum generated by a mass spectrometer, said mass spectrum containing a plurality of peaks each of said plurality of peaks corresponding to a mass-to-charge ratio;

a second storage device operative to maintain computer-executable instructions including a particularly configured computer program to (i) select a plurality of predetermined molecules appropriate to said sample, (ii) create a data set comprising a subset of said plurality of peaks wherein each peak of said subset of said plurality of peaks is assigned to one or more of said plurality of predetermined molecules and differences between measured masses of the plurality of macromolecules are compared to known true masses of the plurality of macromolecules, (iii) apply a robust statistical method to said data set to calculate at least one transformation parameter, the robust statistical method involving the statistical method distinguishing correct estimates from incorrect estimates of data points wherein changing a single data point by an arbitrary amount does not change the result of an associated equation or calculation by an arbitrary amount which results in tolerance of a large number of incorrect data points, and (iv) transform, by self-calibration, said mass spectrum by using said at least one transformation parameter to provide said recalibrated mass spectrum;
a processor in communication with the first and second storage devices and operative to execute the computer program to provide the recalibrated mass spectrum;
an output device in communication with the processor and operative to store or display the recalibrated mass spectrum; and
wherein when the recalibrated mass spectrum is a Quadrupole time of Flight (QTOF) recalibrated spectrum generated by a Quadrupole Time of Flight spectrometer the QTOF recalibrated spectrum having a precision of about 0.005 Da over a mass range of 100-2000 Da.

23. The system of claim 22 wherein the first and second storage devices are combined in a common storage device.

24. The system of claim 22 wherein at least a portion of the second storage device is embedded in memory and combined with the processor in a processor device.

25. A system for providing a recalibrated mass spectrum of a sample including a plurality of macromolecules, the system comprising:
a first storage device operative to maintain a mass spectrum including a plurality of peaks corresponding to a mass-to-charge ratio;
a second storage device operative to maintain computer-executable instructions including a particularly configured computer program to (i) select a plurality of predetermined molecules appropriate to said sample, (ii) create a data set comprising a plurality of peak pairs from said plurality of peaks wherein each of said peak pairs is assigned to one of said plurality of predetermined (iii) apply a robust statistical method to said data set to calculate at least one transformation parameter, the robust statistical method involving the statistical method distinguishing correct estimates from incorrect estimates of data points wherein changing a single data point by an arbitrary amount does not change the result of an associated equation or calculation by an arbitrary amount which results in tolerance of a large number of incorrect data points, and (iv) transform, by self-calibration, said mass spectrum by using said at least one transformation parameter to provide said recalibrated mass spectrum; and
a processor in communication with the first and second storage devices and operative to run the computer program to provide the recalibrated mass spectrum;
an output device in communication with the processor and operative to display the recalibrated mass spectrum.

26. The system of claim 25 wherein the first and second storage devices are combined in a common storage device.

27. The system of claim 25 wherein at least a portion of the second storage device is embedded in memory and combined with the processor in a processor device.

* * * * *